(12) United States Patent
Choi

(10) Patent No.: US 8,936,570 B2
(45) Date of Patent: Jan. 20, 2015

(54) SAFETY SYRINGE

(76) Inventor: Suk Yeo Choi, Daejeon (KR)

(*) Notice: Subject to any disclaimer, the term of this patent is extended or adjusted under 35 U.S.C. 154(b) by 268 days.

(21) Appl. No.: 12/991,428

(22) PCT Filed: Jan. 15, 2009

(86) PCT No.: PCT/KR2009/000208
§ 371 (c)(1),
(2), (4) Date: Nov. 5, 2010

(87) PCT Pub. No.: WO2009/136687
PCT Pub. Date: Nov. 12, 2009

(65) Prior Publication Data
US 2011/0066115 A1  Mar. 17, 2011

(30) Foreign Application Priority Data

May 6, 2008 (KR) .................... 20-2008-0005937 U

(51) Int. Cl.
*A61M 5/00* (2006.01)
*A61M 5/32* (2006.01)
*A61M 5/50* (2006.01)

(52) U.S. Cl.
CPC ....... *A61M 5/322* (2013.01); *A61M 2005/3224* (2013.01); *A61M 2005/3231* (2013.01); *A61M 2005/5073* (2013.01)
USPC ............................ 604/110; 604/240; 604/195

(58) Field of Classification Search
CPC .................... A61M 5/322; A61M 2005/3224; A61M 2005/3223; A61M 5/3202; A61M 2005/3206; A61M 5/3234; A61M 5/3278; A61M 5/3135; A61M 2005/3249; A61M 5/50
USPC ........................ 604/110, 218, 222, 229, 240
See application file for complete search history.

(56) References Cited

U.S. PATENT DOCUMENTS 4,826,489 A * 5/1989 Haber et al. .................. 604/195
4,986,813 A * 1/1991 Blake et al. .................. 604/110
(Continued)

FOREIGN PATENT DOCUMENTS

| KR | 10-2004-101898 | 12/2004 |
| KR | 20-0423645 | 8/2006 |
| KR | 10-0629274 | 9/2006 |

OTHER PUBLICATIONS

International Search Report for PCT/KR2009/000208 mailed Jun. 15, 2009.

*Primary Examiner* — Kevin C Sirmons
*Assistant Examiner* — William Carpenter
(74) *Attorney, Agent, or Firm* — Revolution IP, PLLC

(57) ABSTRACT

The present invention provides a safety syringe which resolves a problem in the prior art whereby the needle assembly does not engage the plunger properly due to limitations in the syringe protrusion molding. The syringe of the present invention comprises: a cylinder which has a space therein to contain fluid and forms a fluid discharging portion at one end; a plunger which is inserted inside the cylinder and slid in a longitudinal direction; a piston which is associated with the upper portion of the plunger in order to make airtight contact between the plunger and the cylinder; a syringe needle assembly which is equipped at the upper portion of the cylinder and affixes a syringe needle. The syringe needle assembly is inserted into and contained inside the cylinder after use and is then disposed. In the needle assembly, plural needle supports comprising a first connector and a second connector are extended to the lower portion. The plunger has a needle support insertion member at the upper portion so that it cannot be separated after the needle supports of the needle assembly are inserted. When the plunger is retracted, the needle assembly is retracted and contained in the cylinder. In the needle support insertion member, a ring-shaped protrusion is placed at the upper portion, and plural ring-shaped protrusion supports which connect and support the ring-shaped protrusions are formed.

3 Claims, 15 Drawing Sheets

(56) References Cited

U.S. PATENT DOCUMENTS

| | | | |
|---|---|---|---|
| 5,308,329 A * | 5/1994 | Mazur et al. | 604/110 |
| 5,395,346 A * | 3/1995 | Maggioni | 604/195 |
| 5,401,246 A * | 3/1995 | Mazur et al. | 604/110 |
| 5,405,327 A * | 4/1995 | Chen | 604/110 |
| 5,462,531 A * | 10/1995 | Novacek et al. | 604/110 |
| 5,540,660 A * | 7/1996 | Jenson | 604/110 |
| 5,578,015 A * | 11/1996 | Robb | 604/195 |
| 5,716,341 A * | 2/1998 | Saito | 604/110 |
| 5,997,511 A * | 12/1999 | Curie et al. | 604/195 |
| 6,117,113 A * | 9/2000 | Novacek et al. | 604/195 |
| 6,193,695 B1 * | 2/2001 | Rippstein, Jr. | 604/195 |
| 6,342,045 B1 * | 1/2002 | Somers | 604/110 |
| 6,530,903 B2 * | 3/2003 | Wang et al. | 604/195 |
| 6,761,707 B2 * | 7/2004 | Huang et al. | 604/240 |
| 6,827,704 B1 * | 12/2004 | Hou | 604/110 |
| 7,572,247 B2 * | 8/2009 | Smith et al. | 604/195 |
| 7,972,301 B2 * | 7/2011 | Oliver | 604/110 |
| 2003/0028151 A1 * | 2/2003 | Righi et al. | 604/218 |
| 2003/0083627 A1 * | 5/2003 | Chen | 604/240 |
| 2003/0093038 A1 * | 5/2003 | Chiang | 604/240 |
| 2003/0212371 A1 * | 11/2003 | Smith et al. | 604/229 |

* cited by examiner

SAFETY SYRINGE

RELATED APPLICATIONS

This application is a 371 application of International Application No. PCT/KR2009/000208, filed Jan. 15, 2009, which in turn claims priority from Korean Patent Application No. 20-2008-0005937, filed May 6, 2008, both of which are incorporated herein by reference in their entireties.

TECHNICAL FIELD

The present invention relates to a safety syringe, and in particular to a safety syringe which advantageously overcomes the problems encountered in the conventional art that a needle support is not accurately fixed to a plunger due to a certain design limit occurring in the course of a molding process in a conventional safety syringe in which a needle is pushed into a cylinder for disposal as a waste.

BACKGROUND ART

A disposable type syringe is generally provided for preventing a secondary infection of disease which occurs due to the reuse of a syringe. The reuse of a syringe is legally prohibited, so the syringe used once is subject to disposal as a waste. The disposable type syringe should be disposed with a cap being covered on the tip of a needle.

However, a user might be hurt by a needle when covering a cap on the tip of a needle in the course of disposal. In addition, a waste disposal worker might be hurt by a needle as a cap is disengaged from the tip of a needle in the course of disposal. A medical worker or a syringe waste disposal worker might be hurt by a needle which was used once, so the hurt worker might be infected by the blood of a patient. This kind of medical accident is frequently reported in the medical field.

In order to overcome the above problems, the applicant of the present invention has filed Korean utility model registration number 0391370 and Korean utility model registration number 0423645 in which the needle of a syringe used once is inputted into a cylinder for disposal as a waste.

According to the Korean utility model registration numbers 0391370 and 0423645, since a needle support is not accurately fixed to a plunger in the course that a needle is being inputted into a cylinder, so a needle is not fully inputted into a cylinder.

FIG. 1 is a cross sectional view of a conventional safety syringe and FIG. 2 is a partially enlarged view illustrating a state that a needle support is is caught by a plunger in a conventional safety syringe.

The conventional safety syringe comprises a needle support 5 which fixedly supports a needle 4 and is formed of a plurality of engaging legs 50 at a lower side of the same, with each engaging leg 50 being equipped with a first connector 51 and a second connector 52 at its lower side. The first connector 51 is fixed in contact with a first engaging shoulder 14 of an upper side of the cylinder 1 so that the needle support 5 is not inwardly pushed into the cylinder 1 in the course of use of a syringe. The second connector 52 is an engaging member for being fixedly caught by a needle support insertion member 24 of an upper side of a plunger 2 so that the needle 4 is inputted into the inner side of the cylinder 1 and is accommodated therein when disposing the cylinder after use.

Namely, a needle support insertion member 24 is formed at an upper side of the plunger 2 for receiving engaging legs 50, so that the engaging legs 50 of the needle support 5 are accommodated therein. A second engaging shoulder 24a is formed at an inner side of the needle support insertion member 24 and is fixedly engaged by a second connector 52 of a lower side of the engaging leg 50. When the plunger 2 moves backwards, the needle support 5 is pulled with the aid of an engagement between the second connector 52 and the second engaging shoulder 24a and is inputted into the inner side of the cylinder.

However, in the above conventional safety syringe, the second engaging shoulder 24a formed at an inner side of the needle support insertion member 24 is formed roughly, not formed accurately, so that it is impossible to obtain a stable engaging state with the second connector 52 formed at the needle support 5, whereby the engaged state is loosened and disengaged for thereby allowing the needle support 5 not to input into the interior of the cylinder.

The problems that the second engaging shoulder 24a formed at an inner side of the needle support insertion member 24 are formed roughly, not formed accurately is due to a design limit in the course of a molding process.

FIG. 3 is a view illustrating an example for describing a molding process for molding a conventional safety syringe and FIG. 4 is a view illustrating an example for describing the problems that a second engaging shoulder is formed roughly, not formed accurately in a conventional safety syringe.

In the molding process of a conventional safety syringe, a plastic liquid is injected into a mold A is solidified and the mold A is separated. According to the conventional safety syringe, the second engaging shoulder 24a at the inner side of the needle support insertion member 24 might be disadvantageously damaged or worn out while the mold A is being separated.

The damaged or worn-out second engaging shoulder 24a does not form a stable engaging relationship with the second connector 52, so that the needle support 5 is not reliably inputted into the inner side of the cylinder.

Technical Problem

Accordingly, it is an object of the present invention to provide a safety syringe which overcomes the problems encountered in the conventional art.

It is another object of the present invention to provide a safety syringe of which an engaging member of a needle support insertion member is not worn-out and damaged in such a manner that one side of a needle support insertion member to which an engaging leg of a needle support is accommodated and engaged is formed in an open shape, with a mold being separated in both directions in the course of a molding process.

Technical Solution

To achieve the above objects, in a safety syringe which comprises a cylinder having a space in its interior for storing a certain fluid with a fluid discharging portion being formed at one side of the same, a plunger which is inserted in an inner side of the cylinder and slides therein in a vertical direction, a piston which is engaged to an upper side of the plunger so that the plunger can be in airtight contact with the cylinder, and a needle support which is engaged at an upper side of the cylinder and fixes a needle, there is provided a safety syringe characterized in that the needle support is inputted into the interior of the cylinder for disposal as a waste after syringe is used, with a plurality of engaging legs equipped with a first connector and a second connector being extended from the needle support, and a needle support insertion member is formed at an upper side of the plunger for preventing an engaging leg of the needle support from being disengaged after the engaging leg is inserted, with the needle support insertion member being accommodated in an inner side of the cylinder as the needle support moves backward when the plunger moves backward, and the needle support insertion member is formed at an upper side of the ring-shaped engaging ring, and a plurality of ring-shaped protrusion supports are vertically formed for connecting and supporting the engaging ring, respectively.

The needle support insertion member is open at its one side, and an injection through hole is formed between the neighboring ring-shaped protrusion supports for allowing a mold A from being easily separated via the same in the course of a molding process.

The engaging ring is configured to easily guide so that the engaging leg of the needle support can be inwardly inserted, and the engaging ring is configured with its diameter getting narrower from an upper side to a lower side at its inner circumferential surface.

Advantageous Effects

The safety syringe according to the present invention has the following advantageous effects.

First, a secondary infection of disease can be prevented by preventing the reuse of a syringe used once.

Second, a needle used once is inputted into a cylinder and is discarded for disposal for thereby disposing the needle in safe.

Third, a plunger is separated and discarded as a waste when disposing a syringe for thereby significantly reducing the volume of wastes.

Fourth, it is possible to enhance the reliability of a safety syringe by overcoming the problems encountered in the conventional art that a needle support is not accurately engaged to a plunger due to a design limit of a molding process.

BRIEF DESCRIPTION OF THE DRAWINGS

The present invention will become better understood with reference to the accompanying drawings which are given only by way of illustration and thus are not limitative of the present invention, wherein.

BEST MODE

Figure 1:
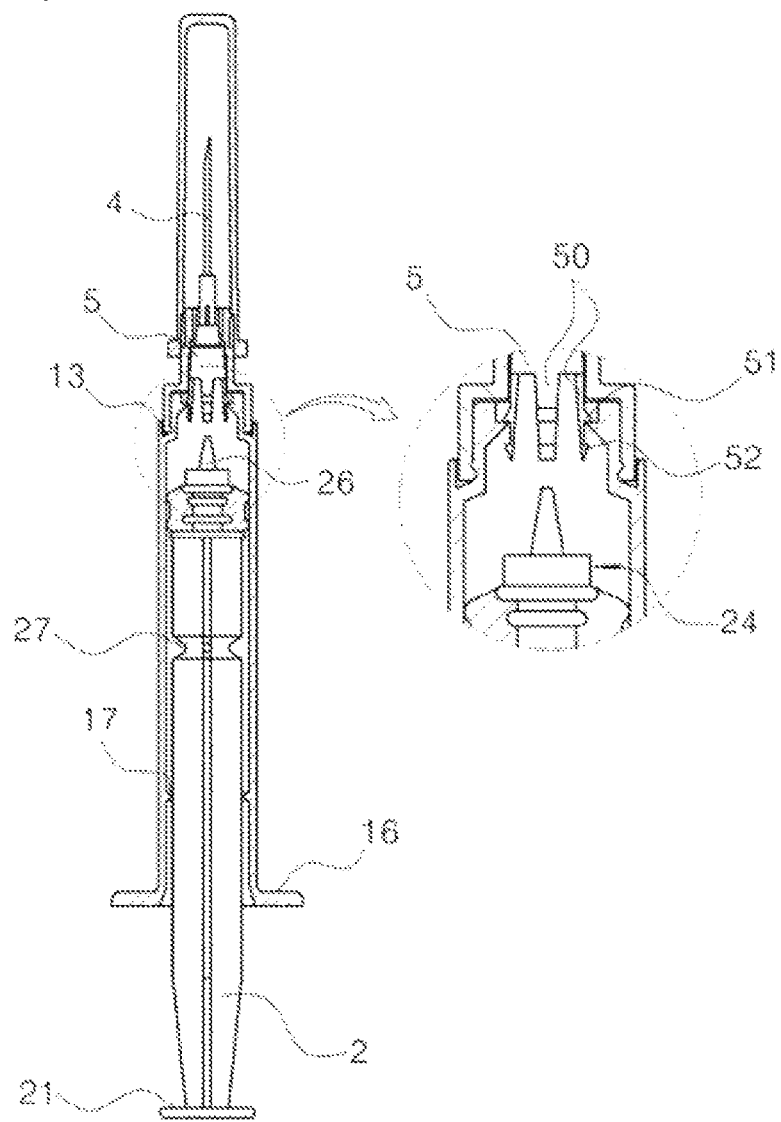
FIG. 1 is a cross sectional view illustrating a conventional safety syringe.
Figure 2:
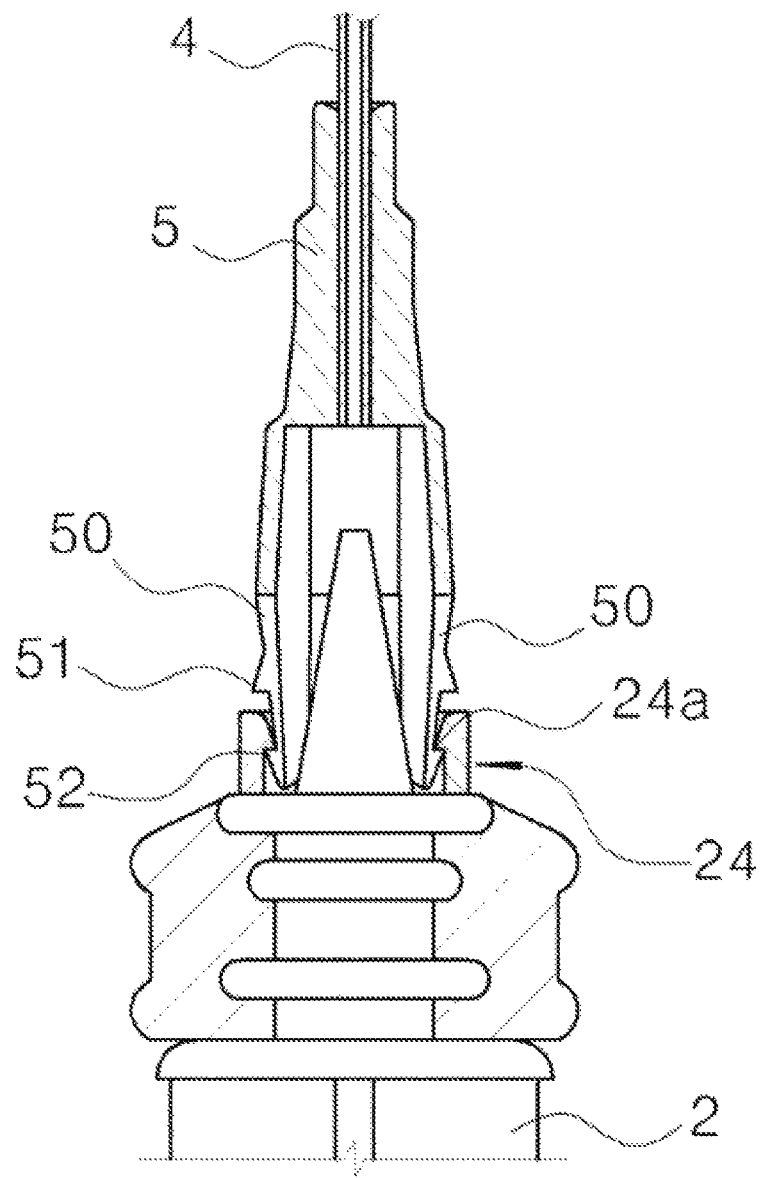
FIG. 2 is a partially enlarged view illustrating a state that a needle support is caught by a plunger in a conventional safety syringe.
Figure 3:
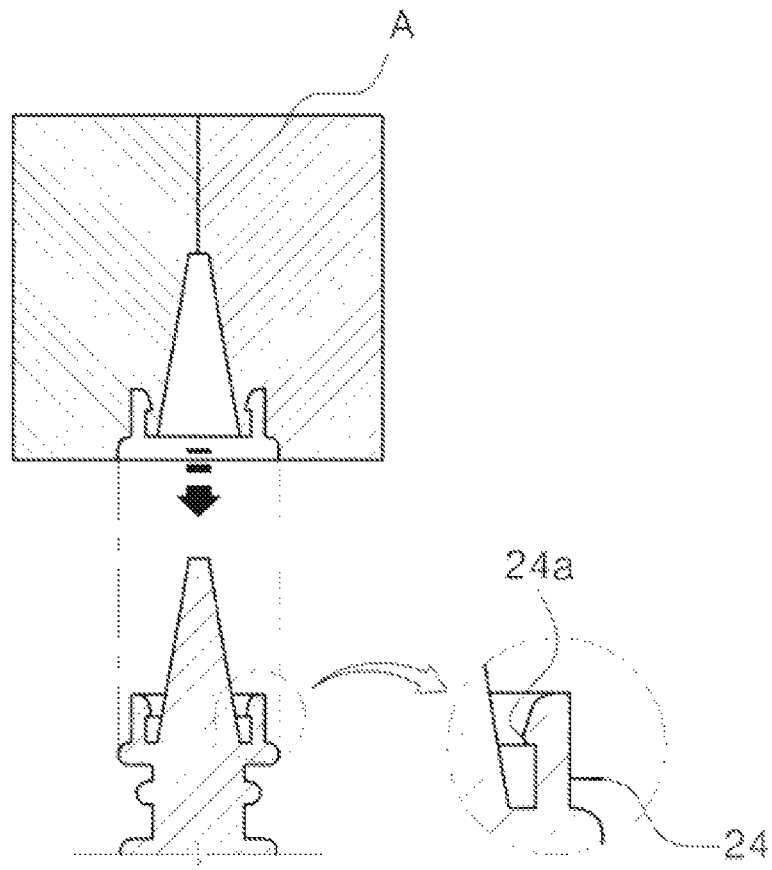
FIG. 3 is a view illustrating an example for describing a molding process for forming a conventional safety syringe.
Figure 4:
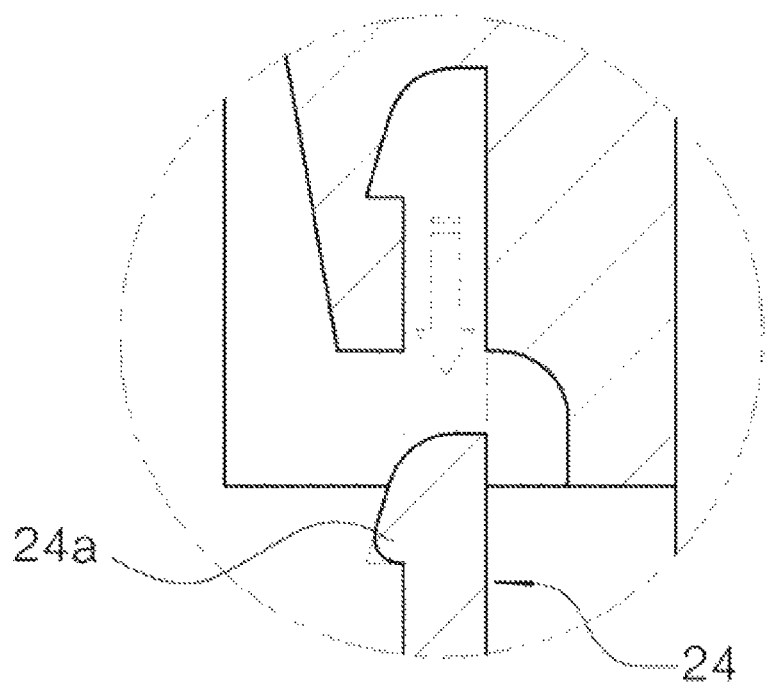
FIG. 4 is a view illustrating an example for describing a problem that a second engaging shoulder is formed roughly in a conventional safety syringe.

The procedure of use of a safety syringe according to an embodiment of the present invention will be described.

A needle protection cap 6 covered for protecting a needle 4 is separated, and a fluid is sucked into a cylinder 1 by inputting a tip of the needle 4 into a fluid. A plunger 2 inserted in the cylinder 1 is pulled toward an opening 15 for thereby generating a suction force by a piston 3 which remains in sealing contact with the cylinder 1. In the course of injection medication, a tip of the needle 4 of the syringe with a fluid therein is injected into a skin of a patient. When a plunger 2 of the syringe is pushed toward a fluid discharging portion 11, the pressure in the cylinder 1 increases and the fluid is discharged through a tip of the needle 4. Since the procedure of use of the syringe is same as the conventional at, the description thereon will be omitted.

Figure 13:
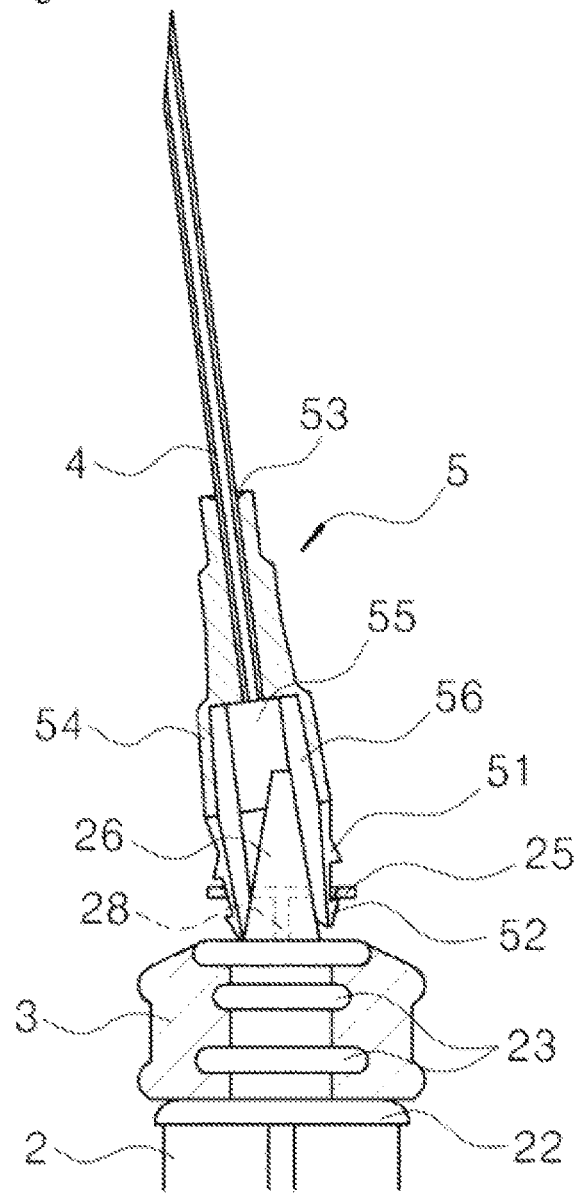
FIG. 13 is a partial cross sectional view illustrating a schematic construction that a needle support and a needle support insertion member are engaged according to an embodiment of the present invention.
Figure 14:
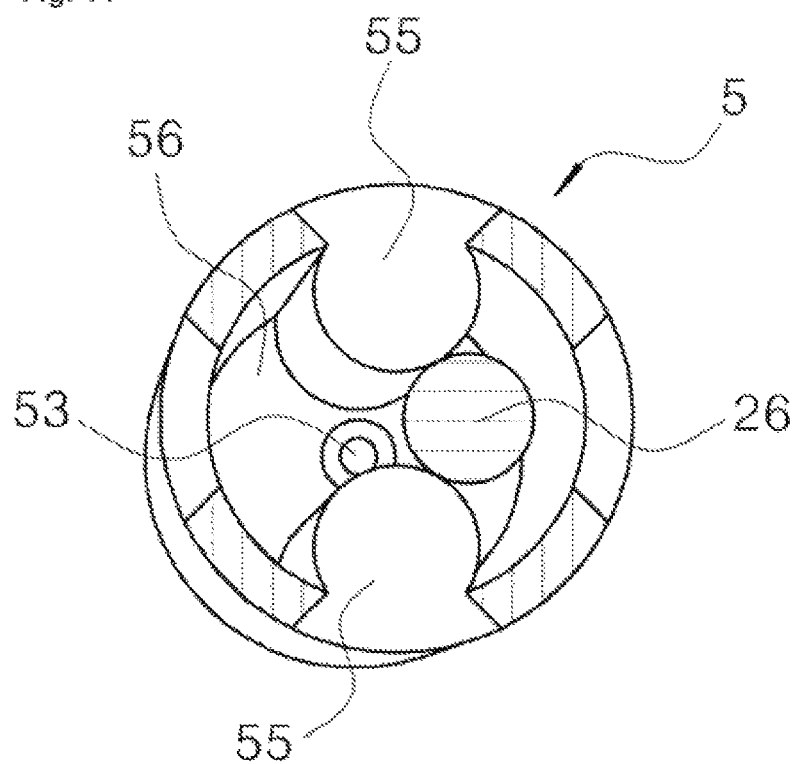
FIG. 14 is a partial cross sectional view illustrating a lower side profile that a center pin is engaged to a center pin engaging groove of a needle support according to an embodiment of the present invention.
Figure 15:
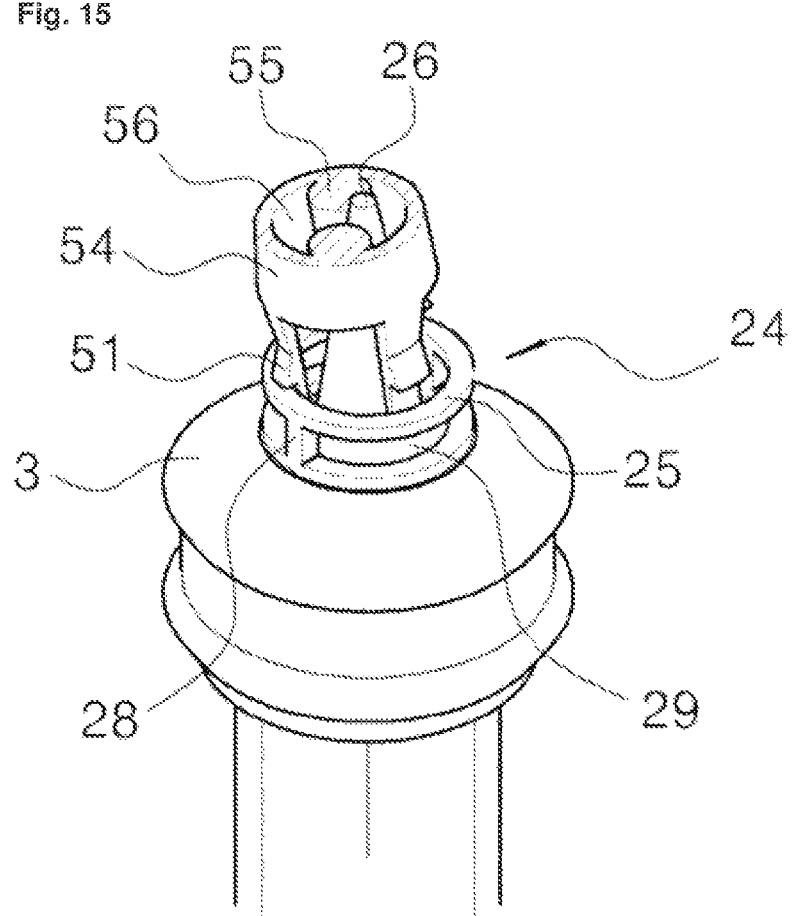
FIG. 15 is a perspective view illustrating a partial cross sectional profile of a needle support according to an embodiment of the present invention.

FIG. 13 is a partial cross sectional view illustrating a schematic construction that a needle support and a needle support insertion member are engaged according to an embodiment of the present invention, and FIG. 14 is a partial cross sectional view illustrating a lower side profile that a center pin is engaged to a center pin engaging groove of a needle support according to an embodiment of the present invention, and FIG. 15 is a perspective view illustrating a partial cross sectional profile of a needle support according to an embodiment of the present invention.

As shown therein, the plunger 2 comes in contacts with a needle support insertion member 24 provided above the plunger 2 and a plurality of fixing legs 50 provided at the needle support 5 before the plunger 2 comes in contact with the fluid discharging portion 11 of the cylinder 1 while the fluid filled in the cylinder 1 of a syringe is discharged to the outside. Here, when the plunger 2 is further pushed, a plurality of the engaging legs 50 made of a plastic material are inserted into the needle support insertion member 24 while receiving inwardly gathering force. The second connector 52 formed at a lower side of the engaging legs 50 is caught by an engaging ring 25 at the side of the needle support insertion member 24 to the extent that it does not escape. The first connector 51 formed at an upper side of the engaging leg 50 is separated from the first engaging shoulder 14 at the side of the cylinder 1 while the engaging legs 50 are bent and gathered into the needle support insertion member 24. Preferably, the second connector 52 formed at a lower side of the engaging leg 50 is formed in a slanted shape which is getting narrower in a downward direction so that the engaging legs 50 can be easily inserted into the needle support insertion member 24.

A conical center pin 26 having a certain length is formed at a center of the needle support insertion member 24. The center pin 26 is engaged with a center pin engaging groove 56 formed at a lower surface of the needle support 5. Two eccentric guide protrusions 55 are opposite to each at the center pin engaging groove 56, so the center pin 26 is not engaged to the center of the center pin engaging groove 56, but is engaged at one side where the eccentric guide protrusion 55 exists. Namely, the interval between the eccentric guide protrusions 55 is less than a diameter of the lower side of the conical center pin 26, so the conical diameter portion of the center pin 26 is caught by the eccentric guide protrusion 55, with the conical shape getting wider in a direction, when the center pin 26 is inserted into the center pin engaging groove 56, and the center pin 26 slides in another direction where the eccentric guide protrusion 55 does not exist, and is eccentrically engaged with the center pin engaging groove 56. The needle support 5 is bent in the opposite direction that the center pin 26 is inserted. The needle support 5 is fixed at the needle fixing cap 6 of the cylinder 1 unless the plunger 2 is pulled in the direction of the opening 15 with only the bending force being applied.

Figure 16:
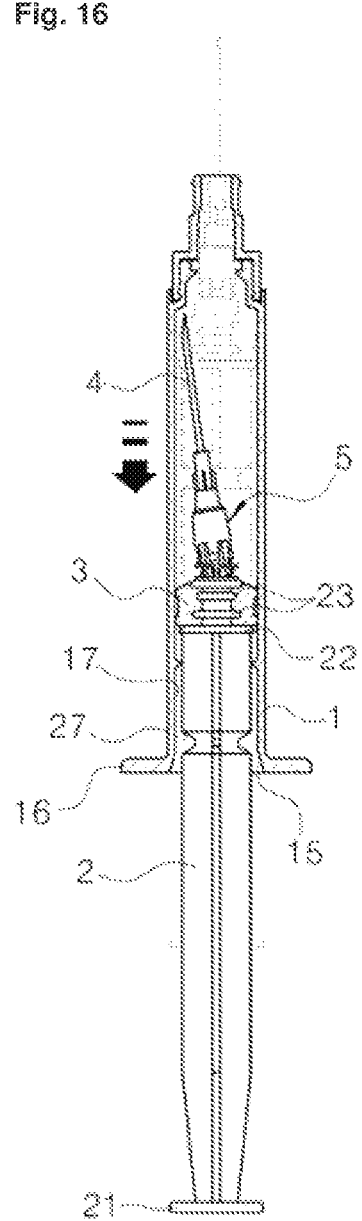
FIG. 16 is a schematic view illustrating an operation state that a needle support is inputted into an inner side of a cylinder according to an embodiment of the present invention.

FIG. 16 is a schematic view illustrating an operation state that a needle support is inputted into an inner side of a cylinder according to an embodiment of the present invention.

As shown therein, when the plunger 2 is pulled in the direction of the opening 15, since the engaging ring 25 of the needle support insertion member 24 and the second connector 52 of the engaging ring 50 are engaged with each other, the needle support 5 is inserted into the inner side of the cylinder 1 depending on the direction of the plunger 2 which is pulled.

The needle support inserted into the cylinder 1 is engaged in an eccentric state deviating from the center with the aid of the eccentric guide protrusion 55 when the center pin 26 of the plunger 2 is engaged to the center pin engaging groove 56, so the needle support 5 including the needle 4 is bent in the direction of an inner wall of the cylinder 1. Namely, even when the plunger 2 is pushed again, the needle 4 does not escape to the outside.

Figure 17:
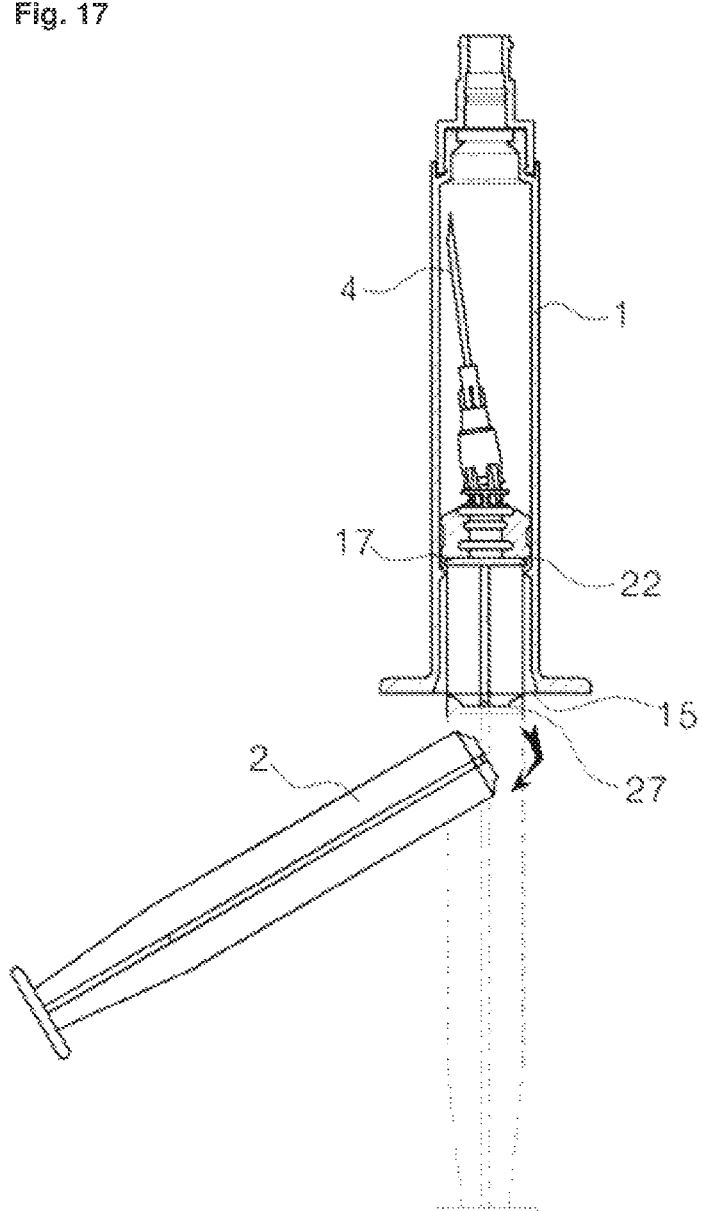
FIG. 17 is a schematic view illustrating an operation that a plunger is cut in the course of disposal of a safety syringe according to an embodiment of the present invention.

FIG. 17 is a schematic view illustrating an operation that a plunger is cut in the course of disposal of a safety syringe according to an embodiment of the present invention.

With the above advantageous construction, it is possible to significantly reduce the volume of the syringe when disposing the same after the needle support 5 is inputted into the cylinder 1, and the plunger 2 can be cut by means of a plunger cutting groove 27 formed at the plunger 2 so that the plunger 2 does not tend to be inserted into the interior again for a reliable disposal.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

MODES FOR CARRYING OUT THE INVENTION

The preferred embodiments of the present invention will be described with reference to the accompanying drawings.

Figure 5:
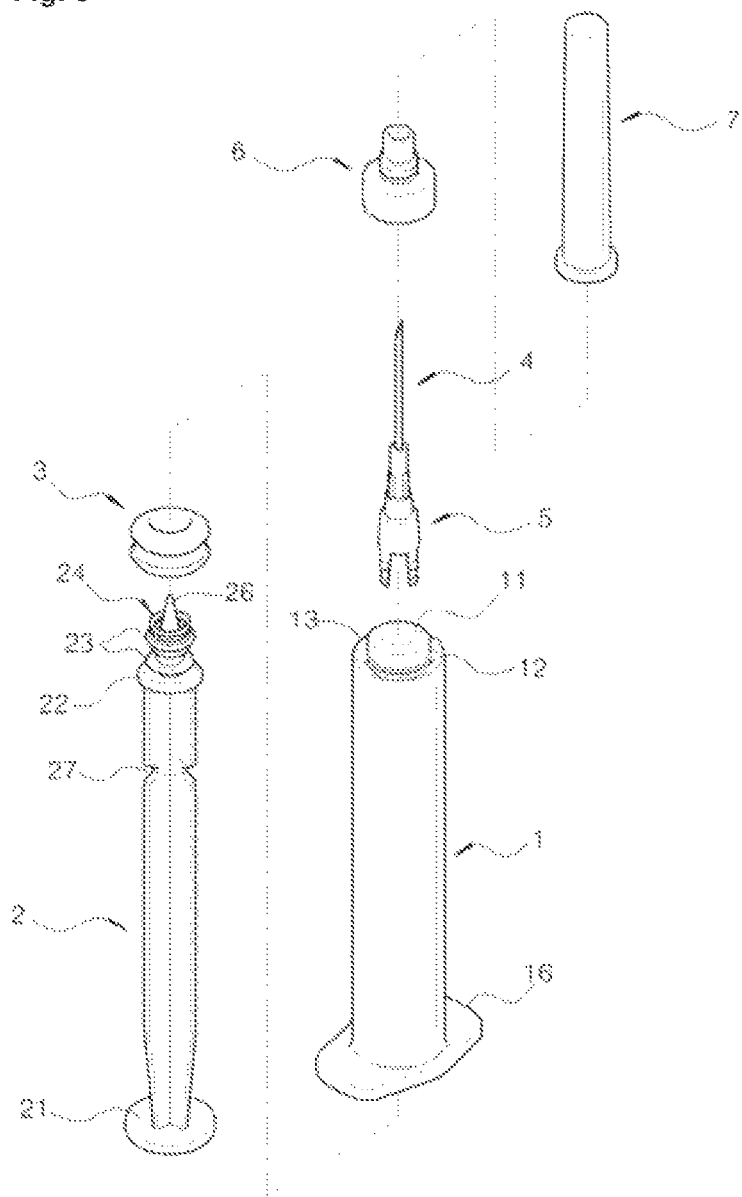
FIG. 5 is a disassembled perspective view illustrating a schematic construction of a safety syringe according to an embodiment of the present invention.
Figure 6:
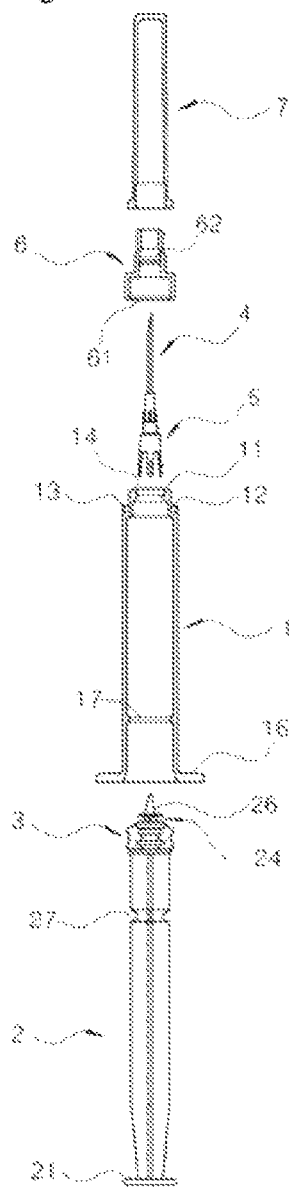
FIG. 6 is a disassembled front cross sectional view illustrating a safety syringe according to an embodiment of the present invention.
Figure 7:
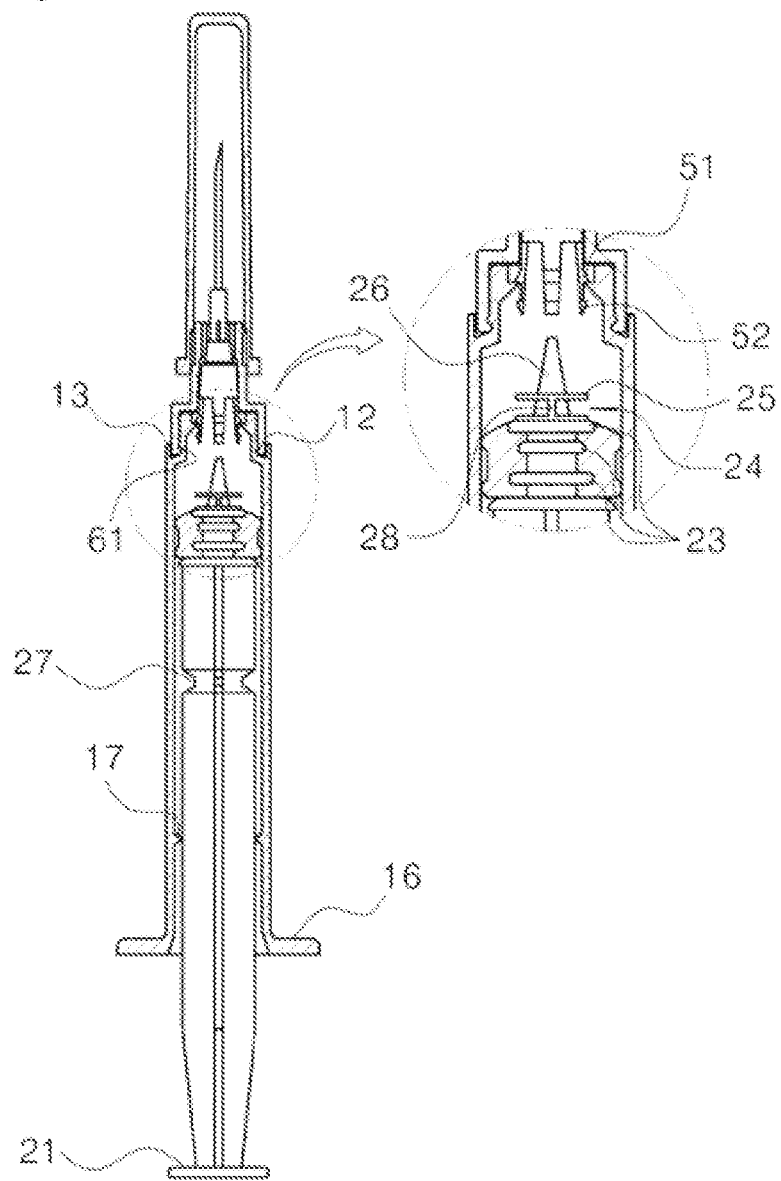
FIG. 7 is a front cross sectional view illustrating an assembled state of a safety syringe according to an embodiment of the present invention.

FIG. 5 is a disassembled perspective view illustrating a schematic construction of a safety syringe according to an embodiment of the present invention, and FIG. 6 is a disassembled front cross sectional view illustrating a safety syringe according to an embodiment of the present invention, and FIG. 7 is a front cross sectional view illustrating an assembled state of a safety syringe according to an embodiment of the present invention.

As shown in FIGS. 5 through 7, the safety syringe according to the present invention comprises a cylindrical cylinder 1 having a space in its interior, a plunger 2 which is inserted in an inner side of the cylinder 1 and slides in a longitudinal direction of the cylinder 1, a piston 3 which is engaged at an upper side of the plunger 2 and is in airtight contact with the cylinder 1, a needle support 5 which fixes a needle 4 and is formed of a plurality of engaging legs 50, a needle fixing cap 6 which provides an engaging member so that the needle support 5 can be fixed at the cylinder 1, and a needle protection cap 7 for covering a tip of the needle so that the needle 4 is not exposed to the outside when not in use.

The cylinder 1 is formed in a cylindrical shape with a space in its interior, with a fluid discharging portion 11 being formed at one side for discharging fluid to the outside, with an opening 15 being formed at the other side for a user to push and pull the plunger 2, so that the plunger 2 can slide in the cylinder 1 in a longitudinal direction.

The fluid discharging portion 11 has a diameter less than an outer diameter of the cylinder 1 and has a function for discharging the fluid filled in the cylinder 1 to the outside and is protruded from the upper side of the cylinder 1. A first engaging portion 12 is formed at a circumferential surface of the fluid discharging part 11 and is formed of a protrusion and a groove for engaging the needle fixing cap 6. FIG. 14 is an enlarged cross sectional view illustrating the major elements of a cylinder and a needle fixing cap according to an embodiment of the present invention.

A movement prevention part 13 extended by a certain length with the same diameter as the outer diameter of the cylinder 1 is formed around the needle fixing cap 6 for preventing the needle fixing cap 6 from moving after the first engaging part 12 and the needle fixing cap 6 are engaged.

The first engaging shoulder 14 is formed at a certain inner portion of the fluid discharging portion 11 formed at the upper side of the cylinder 1 while being in contact with the first connector 51 of the needle support 5 so that the needle support 5 does not go into the cylinder 1 in a state that the needle support 5 is positioned at the upper side of the cylinder 1.

A flange 16 is protruded from around the opening 15 of the cylinder 1 for a finger to hook. Fluid is being injected with a thumb pushing a lower plate 21 of the plunger 2, with an index finger and a middle finger being hooked on the flange 12 of the cylinder 1, so that the cylinder 1 does not move back in the course of fluid injection.

When fluid such s injection or blood is sucked into the cylinder 1, it is needed to pull the plunger 2 in the cylinder 1. At this time, an escape prevention shoulder 17 is formed close to the opening 15 at the inner side of the cylinder 1 so that the plunger 2 does not separate from the cylinder 1. The escape prevention shoulder 17 is to be engaged with an upper plate 2 formed at an upper side of the plunger 2 when the plunger 2 is being pulled.

Here the plunger 2 is inserted in the inner space of the cylinder 1 and slides therein for thereby storing a certain fluid into the space of the cylinder 1 or discharging the stored fluid to the outside of the cylinder 1.

A piston 3 is engaged at an upper side of the plunger 2 while being airtight contact with the cylinder 1 for thereby generating a suction force or a compression force when sucking the fluid into the cylinder 1 or discharging the fluid. A piston fixing protrusion 23 is provided at a portion where the piston 3 is engaged to the plunger 2 so that the piston 3 engaged to the plunger 2 does not disengage from the plunger 2.

The piston 3 is engaged to an upper side of the plunger 2 with a needle support insertion member 24 being formed at its center portion for guiding the needle support 5 into the cylinder 1. With the above advantageous construction, the needle 4 used and the needle support 5 are inputted into the cylinder 1 for disposal, so it is possible to prevent a secondary infection of disease which is one the important feature of the present invention.

Figure 8:
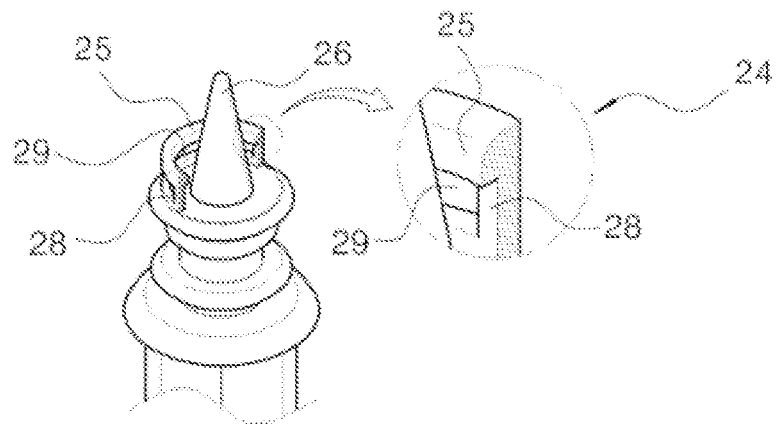
FIG. 8 is an enlarged perspective view illustrating a needle support insertion member of a safety syringe according to an embodiment of the present invention.

The needle support insertion member 24 is like an engaging means for preventing the engaging leg 50 of the needle support 5 from being disengaged after it is inputted, with a ring-shaped protrusion 25 being formed at its upper side and engaged with the second connector 52 of the engaging leg 50, with a pair of ring-shaped protrusion supports 28 being vertically formed for connecting the upper side of the plunger 2 and the engaging ring 25 for stably supporting the engaging ring 25. FIG. 8 is an enlarged perspective view illustrating the needle support insertion member of the safety syringe according to an embodiment of the present invention.

As shown therein, the needle support insertion member 24 is configured as a pair of ring-shaped protrusion supports 28 are upright installed with two sides of the same being opposite to each other. The engaging ring 25 is connected to an upper side of the ring-shaped protrusion support 28. One open side of the needle support insertion member 24 corresponds to an injection through hole 29 for allowing a mold A to separate in the course of a molding process, so the molding process can be reliably performed without damaging a lower surface of the engaging ring 25 with the aid of the molding method in which the mold A is separated from a side surface for thereby forming a reliable engaging structure for the second connector 52.

Figure 9:
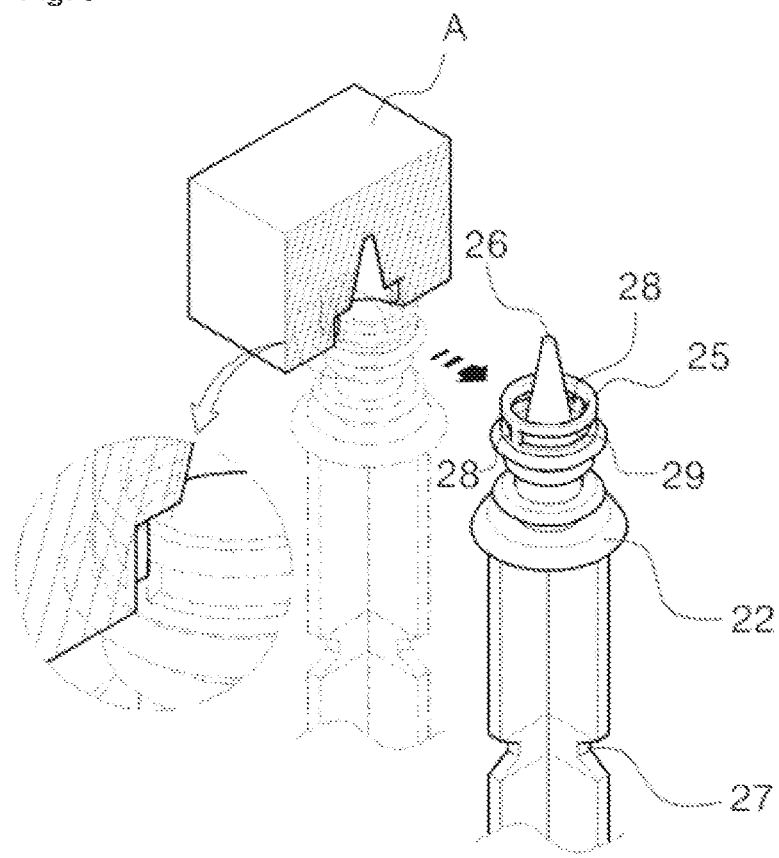
FIGS. 9 and 10 are schematic views illustrating a molding process of a safety syringe according to an embodiment of the present invention.
Figure 10:
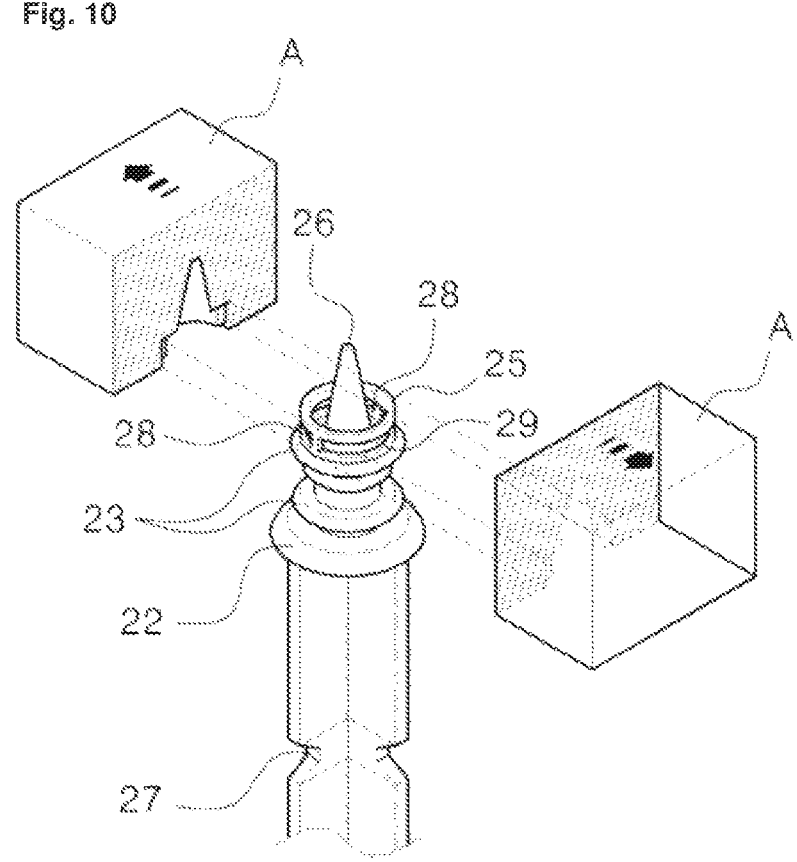

FIGS. 9 and 10 are schematic views illustrating a molding process of a safety syringe according to an embodiment of the present invention. As shown therein, the mold A is separated in two directions according to an embodiment of the present invention for thereby forming an accurate angle at a lower side of the engaging ring 25. As a result, it is possible to prevent the damage of an engaging means which might occur in the conventional art that the needle support insertion member 24 is forcibly pulled out in a vertical direction in the course of the conventional molding process.

As shown in FIG. 8 which shows the engaging ring 25, the engaging leg 50 of the needle support 5 is formed in a certain shape for allowing the engaging leg 50 to be easily inputted in an inward direction. The inner circumferential surface of the engaging ring 25 is formed with its diameter getting narrower from the upper side to the lower side. Preferably, the cross section of the engaging ring 25 is formed in an inwardly slanted triangle shape or an inwardly bent hand fan shape.

The lower surface of the engaging ring 25 is flat with a corner portion where the lower surface and the inner surface meet with each other being at a sharp angle, not being randomly rough, so it is possible to obtain a reliable engaging relationship between the second connector 52 of the engaging leg 50 and the engaging ring 25.

The conical center pin 26 is protruded from a center of the needle support insertion member 24 with a certain length, and the center pin 24 is inserted into the center pin engaging groove 56 formed at the needle support 5 when the needle support 5 and the plunger 2 are engaged with each other. At this time, an eccentric engagement is possible at the center of the needle support 5 with the aid of an eccentric guide protrusion 55 formed at an inner side of the center pin engaging groove 56. So, the needle support 5 is shaped with its center being slanted in one direction. In a state that the center of the needle support 5 is slanted in one direction, when the needle 4 is inputted into the cylinder 1, the needle 4 is bent toward the wall of the cylinder 1, so that the needle 4 does not escape from the fluid discharging portion 10. The operation that the center pin 26 is eccentrically engaged with the needle support 5 will be described.

A lower plate 21 is formed at a lower side of the plunger 2 in order to help a user apply force to the plunger 2 and push the same in the course that fluid stored in the space of the cylinder 1 is discharged to the outside. An upper plate 22 is disposed at an upper side of the plunger 2 so that the plunger 2 is not separated from the cylinder 1 in the course that the plunger 2 inserted in the cylinder 1 is pulled for sucking fluid. Namely, the plunger 2 is not separated from the cylinder 1 as the upper plate 22 is caught by the escape prevention shoulder 17 of the cylinder 1.

The needle support 5 is inputted into the cylinder 1 via the engaging part 23 of the plunger 2 for thereby reducing the volume of the syringe after it is used, and the plunger 2 is equipped with a plunger cutting groove 27 for cutting the plunger 2 so that the plunger 2 is not inputted into the cylinder 1 for disposal after the syringe is used.

Figure 11:
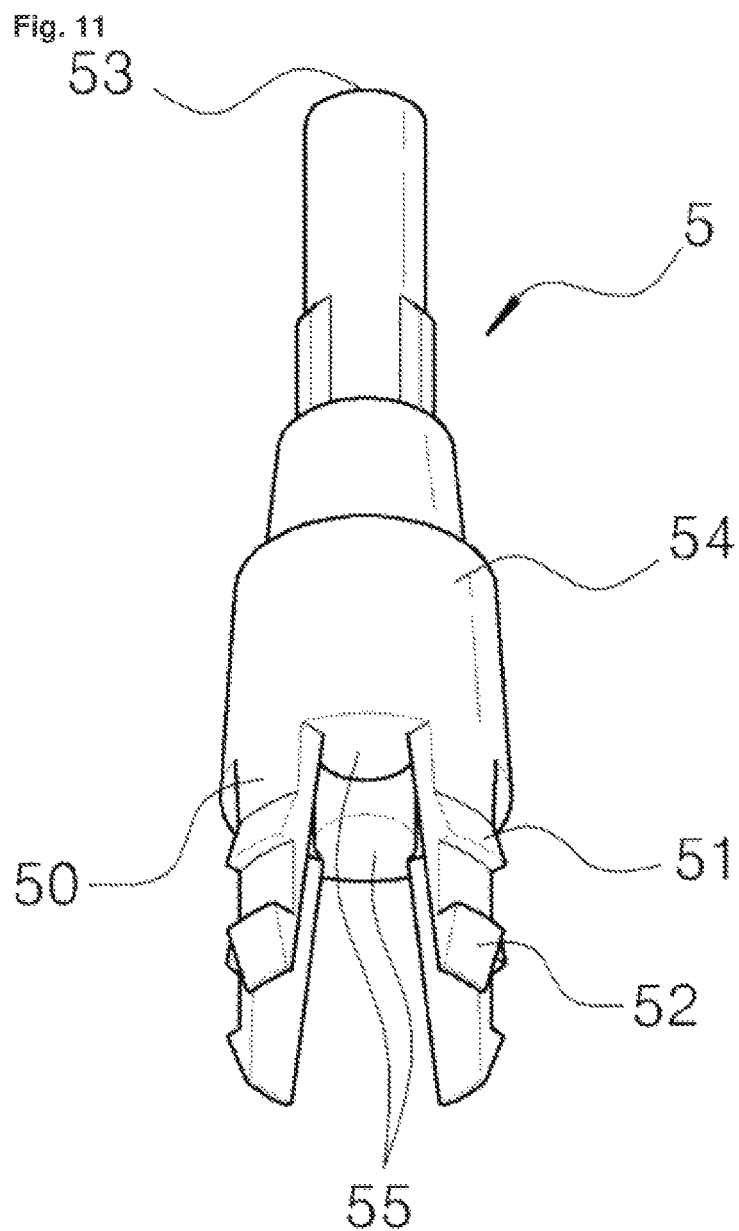
FIG. 11 is a schematic perspective view illustrating a needle support of a safety syringe according to the present invention.

The needle support 5 is to fix the needle 4. FIG. 11 is a schematic perspective view illustrating a needle support of a safety syringe according to the present invention.

A needle engaging groove 53 is formed in a vertical direction at a center of the needle support 5 for thereby fixedly engaging the needle 4. A plurality of engaging legs 50 are formed at a lower side of the needle support 5. The engaging leg 50 is equipped with a first connector 51 and a second connector 52. The first connector 51 is fixed to an upper side of the cylinder 1 while being in contact with the first engaging shoulder 14 of the cylinder 1 when the safety syringe is assembled. The second connector 52 is caught by the engaging ring 25 of the needle support insertion member 24 at the side of the plunger 2 when being inputted into the cylinder 1. Preferably, the number of the engaging legs 50 is four.

A body 54 which connects the needle 4 and the engaging legs 50 in the needle support 5 is formed in a step shape. A center pin engaging groove 56 is formed at a lower surface of the body 54 for engaging with the center pin 26. Two opposite eccentric guide protrusions 55 are provided at the center pin engaging groove 56. The interval between the opposite eccentric guide protrusions 55 is less than the diameter of the lower side of the conical center pin 26. The conical center pin 26 slides in one direction where the eccentric guide protrusion 55 is not formed, and is eccentrically engaged, not being accurately engaged to the center with the aid of the eccentric guide protrusion 55 in the course that the conical center pin 26 is inputted into the center pin engaging groove 56.

The needle fixing cap 6 is a means for fixing the needle support 5 to an upper side of the cylinder 1 and an upper side of the cylinder 1 is separated for a stable fixing.

Figure 12:
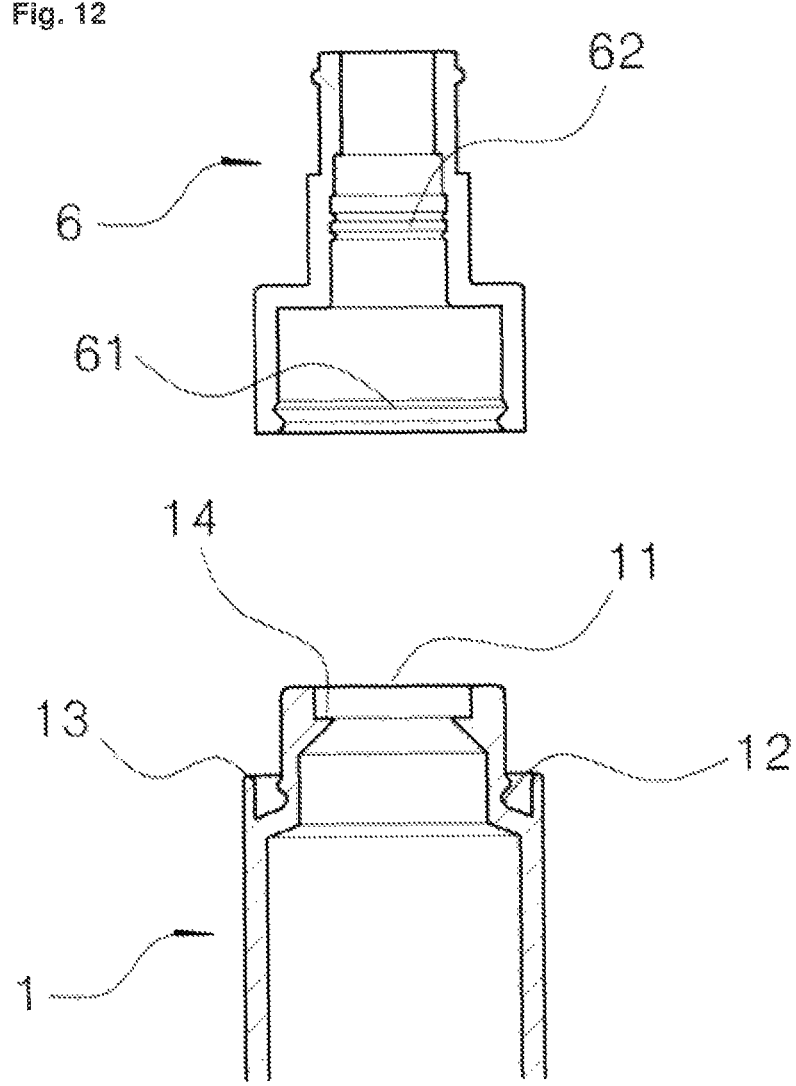
FIG. 12 is an enlarged cross sectional view illustrating major portions of a cylinder and a needle fixing cap according to an embodiment of the present invention.

The needle support 5 is engaged at an inner side of the needle fixing cap 6, and the needle fixing cap 6 is engaged to the body of the cylinder 1. The needle fixing cap 6 is equipped at an inner side with a second engaging part 61 formed of a protrusion and a groove which are engaged with a protrusion and a groove formed at the first engaging part 12 at the side of the cylinder 1, respectively. FIG. 12 is an enlarged cross sectional view illustrating major elements of a cylinder and a needle fixing cap according to an embodiment of the present invention.

A plurality of O-ring shaped protrusions 62 are formed at an inner side of the needle fixing cap 6 when the O-ring material having an airtight function is not provided. The O-ring shaped protrusion 62 has an airtight function while being in airtight contact with the needle support 5.

The needle protection cap 7 is to prevent a user from being hurt by needle when the needle 4 is exposed to the outside and is to protect the needle 4 by covering the cap so that the needle 4 is not bent and does not gather dirt.

INDUSTRIAL APPLICABILITY

As described above, the present invention provides a safety syringe is which is capable of reliably preventing a secondary infection of disease due to the reuse of a syringe, can be disposed in safe. The volume of the syringe wastes can be significantly reduced. A needle support and a plunger can be accurately engaged in the safety syringe according to the present invention.

The invention claimed is:

1. A safety syringe, comprising:
 a cylinder having a space formed therein for storing a certain fluid;
 a plunger inserted in an inner side of the cylinder and slides therein in a vertical direction;
 a piston which surrounds and is engaged with an upper portion of the plunger so that the plunger can be in airtight contact with the cylinder; and
 a needle support which is inserted in an upper side of the cylinder and fixes a needle,
 wherein the needle support has a body to fix the needle and a plurality of engaging legs extending downward from the body, each leg having an engaging protrusion to horizontally and outwardly protrude from the leg,
 wherein a needle support insertion member is formed outside of the piston and plunger so as to extend from a top of the plunger toward the needle support,
 wherein the needle support insertion member has a ring-shaped protrusion and ring-shaped protrusion supports spaced from each other, each ring-shaped protrusion support extending vertically from the top of the plunger toward the needle support,
 wherein the ring-shaped protrusion protrudes horizontally and inwardly from upper portions of the ring-shaped protrusion supports, and
 wherein the engaging protrusions of the engaging legs are caught by the ring-shaped protrusion when the needle support in inputted into the inner side of the cylinder for disposal as a wasted after the syringe has been used,
 wherein a conical center pin having a certain length extends vertically from a center of the needle support insertion member, and a center pin engaging groove is formed at a lower side of the needle support, and two opposite eccentric guide protrusions are formed at an inner side of the center pin engaging groove.

2. The safety syringe of claim 1, wherein injection through holes are formed between the neighboring ring-shaped protrusion supports for allowing a mold to be easily separated via the same in the course of a molding process.

3. The safety syringe of claim 1, wherein the ring-shaped protrusion is configured with an inner diameter thereof getting narrower from a lower side to an upper side.

* * * * *